(12) United States Patent
Schell (10) Patent No.: US 6,606,522 B2
(45) Date of Patent: Aug. 12, 2003

(54) TORQUE MECHANISM AND METHOD FOR ENDOCARDIAL LEADS

(75) Inventor: Jon Schell, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/870,126

(22) Filed: May 30, 2001

(65) Prior Publication Data

US 2002/0183820 A1 Dec. 5, 2002

(51) Int. Cl.⁷ ................................................ A61N 1/00
(52) U.S. Cl. ........................................ 607/122; 607/127
(58) Field of Search ............................ 607/116–138; 600/373–381; 604/527

(56) References Cited

U.S. PATENT DOCUMENTS

| | | | |
|---|---|---|---|
| 4,295,270 A | 10/1981 | Cammarata | 29/828 |
| 4,452,254 A | 6/1984 | Goldberg et al. | 128/785 |
| 4,547,193 A | 10/1985 | Rydell | 604/282 |
| 4,559,951 A | 12/1985 | Dahl et al. | 128/642 |
| 4,699,157 A | 10/1987 | Shonk | 128/786 |
| 5,005,587 A | 4/1991 | Scott | 128/786 |
| 5,014,721 A | 5/1991 | Hirschberg | 128/786 |
| 5,057,092 A | * 10/1991 | Webster, Jr. | 138/123 |
| 5,181,920 A | 1/1993 | Mueller et al. | 606/159 |
| 5,336,254 A | 8/1994 | Brennen et al. | 607/129 |
| 5,397,304 A | 3/1995 | Truckai | 604/95 |
| 5,569,220 A | * 10/1996 | Webster, Jr. | 138/125 |
| 5,591,142 A | * 1/1997 | Van Erp | 604/264 |
| 5,628,774 A | 5/1997 | Helland et al. | 607/116 |
| 5,662,621 A | 9/1997 | Lafontaine | 604/281 |
| 5,674,272 A | 10/1997 | Bush et al. | 607/122 |
| 5,680,860 A | 10/1997 | Imran | 128/642 |
| 5,755,762 A | 5/1998 | Bush | 607/122 |
| 5,814,090 A | 9/1998 | Latterell et al. | 607/36 |
| 5,843,076 A | 12/1998 | Webster, Jr. et al. | 606/41 D |
| 5,843,149 A | 12/1998 | Ebert et al. | 607/116 |
| 5,851,226 A | 12/1998 | Skubitz et al. | 607/126 |
| 5,865,791 A | 2/1999 | Whayne et al. | 604/49 |
| 5,882,346 A | 3/1999 | Pomeranz et al. | 604/280 |
| 5,891,135 A | 4/1999 | Jackson et al. | 606/41 |
| 5,891,136 A | 4/1999 | McGee et al. | 606/41 |
| 5,921,982 A | 7/1999 | Lesh et al. | 606/41 |
| 5,925,038 A | 7/1999 | Panescu et al. | 606/41 |
| 5,931,862 A | 8/1999 | Carson | 607/120 |
| 5,984,917 A | 11/1999 | Fleischman et al. | 606/32 |
| 6,051,017 A | 4/2000 | Loeb et al. | 607/1 |
| 6,055,457 A | 4/2000 | Bonner | 607/126 |
| 6,083,216 A | 7/2000 | Fischer, Sr. | 604/530 |
| 6,122,552 A | 9/2000 | Tockman et al. | 607/116 |
| 6,132,438 A | 10/2000 | Fleischman et al. | 606/139 |
| 6,181,965 B1 | 1/2001 | Leob et al. | 607/3 |
| 6,213,995 B1 | * 4/2001 | Steen et al. | 604/527 |
| 6,217,528 B1 | 4/2001 | Koblish et al. | 600/585 |
| 6,477,428 B1 | 11/2002 | Skinner et al. | 607/122 |

* cited by examiner

Primary Examiner—Mark Bockelman
(74) Attorney, Agent, or Firm—Schwegman, Lundberg, Woessner & Kluth, P.A.

(57) ABSTRACT

A lead assembly includes a flexible lead body which extends from a proximal end to a distal end, the lead body includes one or more conductors therein. The lead assembly further includes a braided torque transmission member, and optionally at least one coating of insulative material coated directly on the torque transmission member.

25 Claims, 4 Drawing Sheets

TORQUE MECHANISM AND METHOD FOR ENDOCARDIAL LEADS

RELATED APPLICATIONS

This application is related to U.S. Patent Application Ser. No. 09/870,369 entitled "LEAD HAVING COMPOSITE TUBING" filed on even date herewith, and U.S. patent application Ser. No. 09/292,715, filed on Apr. 15, 1999, entitled "STEERABLE CORONARY SINUS DEFIBRILLATION LEAD", now U.S. Pat. No. 6,445,958, each of which are incorporated by reference herein.

TECHNICAL FIELD

The present invention relates generally to leads for stimulating or monitoring tissue. More particularly, it pertains to a torque mechanism for an extendable and/or retractable lead.

BACKGROUND

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle.

Cardiac pacing may be performed by the transvenous method or by leads implanted directly onto the epicardium. Permanent transvenous pacing is performed using a lead positioned within one or more chambers of the heart. One or more leads may be positioned in the ventricle or in the atrium through a subclavian vein, and the lead terminal pins are attached to a pacemaker which is implanted subcutaneously.

The lead includes a conductor, such as a coiled conductor, to conduct energy from the pacemaker to the heart, and also signals received from the heart. The lead further includes outer insulation to insulate the conductor. Currently, providing the lead with insulation is done by stringing silicone tubing over the lead. Stringing involves the use of chemicals which swell the silicone tubing, so that the coiled conductor can be pulled through the tubing. As the chemicals evaporate, the tubing contracts around the conductor. Stringing is a complicated manufacturing process which also can result in axial gaps between the conductor and the insulative tubing. The gaps contribute to an increase in the size of the lead body outer diameter.

One approach to implanting the leads permanently or semi-permanently is to include active or passive fixation elements with the leads. Active fixation elements, such as a helix, are rotated to screw the lead into the endocardial wall. To rotate the helix, the coiled conductor is rotated or a rigid stylet is removably disposed within the lead and rotated. As the coil is rotated, however, the shape of the coil opens and closes changing the pitch of the coil, and changing the amount of torque applied to the helix. As the stylet is rotated, the active fixation element sometimes jumps out of the end of the lead, resulting in potential damage to tissue and/or the helix, thereby frustrating the process of implantation. In addition, it is difficult for the implanter to determine how many turns to the stylet are necessary to advance the helix a certain distance.

Accordingly, there is a need for a lead which allows for a less complex manufacturing process and improved insulation. What is also needed is a lead having a smaller outer diameter. What is further needed is a lead which gives the implanter more control over the implantation process.

SUMMARY OF THE INVENTION

A lead assembly is provided which includes an insulative lead body extending from a proximal end to a distal end, and the lead body has one or more conductors disposed therein. The lead assembly further includes an electrode assembly including at least one electrode electrically coupled with the at least one conductor, where the at least one conductor includes at least one braided conductor, and the braided conductor is rotatable to extend and/or retract at least one electrode. At least one coating of insulation is coated directly on the braided conductor.

Several options for the lead assembly are as follows. For instance, in one option, a portion of the at least one coating is removed from the braided conductor to reveal an exposed portion of the braided conductor, and at least one electrode is electrically and mechanically coupled with the exposed portion of the braided conductor. In another option, the lead assembly further includes a second coating of insulation coated between the braided conductor and a second conductor, and the second coating is coated directly on the second conductor. In yet another option, the braided conductor comprises a torque transfer member.

In another embodiment, a lead assembly is provided which includes a flexible lead body extending from a proximal end to a distal end, the lead body including one or more conductors disposed therein, an electrode assembly including at least one electrode electrically coupled with at least one conductor, and a flexible torque transmission member extending from the proximal end to the distal end, the torque transmission member comprising a braided member rotatable to extend and retract a first electrode mechanically coupled thereto.

Several options for the lead assembly are as follows. For instance, in one option, the torque transmission member is non-removably disposed within the lead body. In another option, the lead assembly further includes a coating of insulation coated between a first conductor and a second conductor, where the coating of insulation is optionally coated directly on the first conductor. The lead assembly, in another option, further includes an outer layer of insulative coating, and an inner layer of insulative coating, wherein each insulative coating is coated directly on one of the at least one conductors, and optionally has a stripped portion where a portion of the outer layer is stripped from the conductor.

In yet another embodiment, a lead assembly is provided which includes a flexible, insulative lead body extending from a proximal end to a distal end, the lead body including one or more conductors disposed therein. The lead assembly has an electrode assembly including at least one electrode electrically coupled with at least one conductor. The lead assembly further includes a braided means for transferring torque from the proximal end to a first electrode, the means for transferring torque rotatable within the flexible, insulative lead body to extend and/or retract the first electrode.

Several options for the lead assembly are as follows. For instance, in one option, the torque transmission member is non-removably disposed within the lead body. In another option, the means for transferring torque is operably coupled at the proximal end of the lead body. In yet another option, the lead assembly further includes a first conductor and a second conductor, and a coating of insulation coated between the first conductor and the second conductor. The braided means for transferring torque, in one option, comprises an electrical conductor configured to conduct signals from the proximal end to the first electrode.

In another embodiment, a method is provided which includes braiding material to form a torque transmission member, mechanically coupling the torque transmission member with an extendable and/or retractable electrode, disposing the torque transmission member within a flexible lead body, and rotating the torque transmission member and extending at least one electrode.

Several options for the method are as follows. For instance, in one option, the method further includes coating insulative material directly on the torque transmission member. In another option, braiding the material includes braiding conductive material to form an electrically conductive torque transmission member. The method includes, in another option, braiding flexible material to form a flexible torque transmission member. Still further, in another option, the method further includes providing a conductor over and around the torque transmission member, and coating insulative material directly on the conductor.

In another embodiment, a method is provided and includes braiding two or more flexible conductors to form a first flexible, braided conductor, the first braided conductor extending from a first end to a second end. The method further includes coating insulative material directly on the first braided conductor, mechanically and electrically coupling at least one rotatable electrode with the first braided conductor, and disposing the first braided conductor within an outer insulative lead body. The method further includes rotating the first braided conductor and rotating the rotatable electrode, and coupling the first end of the first conductor with an energy source.

Several options for the method are as follows. For instance, the method optionally includes braiding multiple conductors to form a second conductor around the first flexible, braided conductor, and optionally further coating a second coating of insulative material directly on the second braided conductor. In another option, the method includes stripping insulative material from a portion of the first braided conductor, and exposing a portion of the first braided conductor.

The lead provides for a smaller lead body diameter due to the elimination of gaps, and tolerance stack-up of the assembly. The lead allows for the ability to start and stop tubing to allow for transition areas of the outer insulation, allowing for the device to have an isodiametric shape. Furthermore, the braided conductors have multiple intersections which offer improved flex fatigue properties. A further benefit is that the anode and cathode are not co-radial, the cathode is suitable for use as a driving mechanism for an extendable or retractable positive fixation lead.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
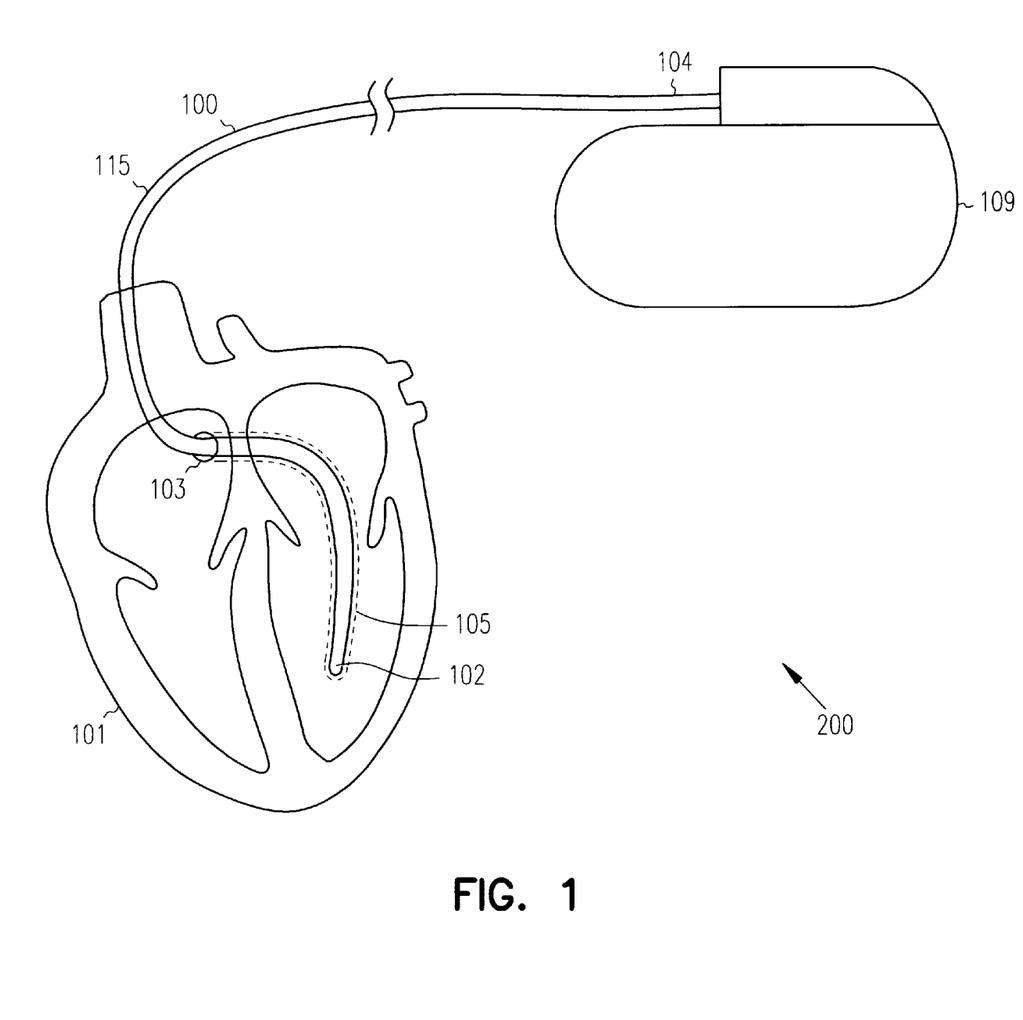
FIG. 1 illustrates a system for monitoring and stimulating the heart constructed in accordance with one embodiment.

FIG. 1 illustrates a system 200 for delivering electrical pulses to stimulate a heart 101 and/or for receiving electrical pulses to monitor the heart 101. The system 200 includes a pulse generator and signal sensor 109 and a lead 100. The lead 100 extends from a distal end 102 to a proximal end 104, and has an intermediate portion 106 therebetween. The distal end 102 is adapted for implantation within the heart of a patient and the proximal end 104 has a terminal connector which electrically connects the various electrodes and conductors within the lead body 115 to a pulse generator and signal sensor 109. The pulse generator and signal sensor 109 contains electronics to sense various electrical signals of the heart and also produce current pulses for delivery to the heart 101. The pulse generator and signal sensor 109 is implanted pectorally, abdominally, or elsewhere within the patient.

Figure 2:
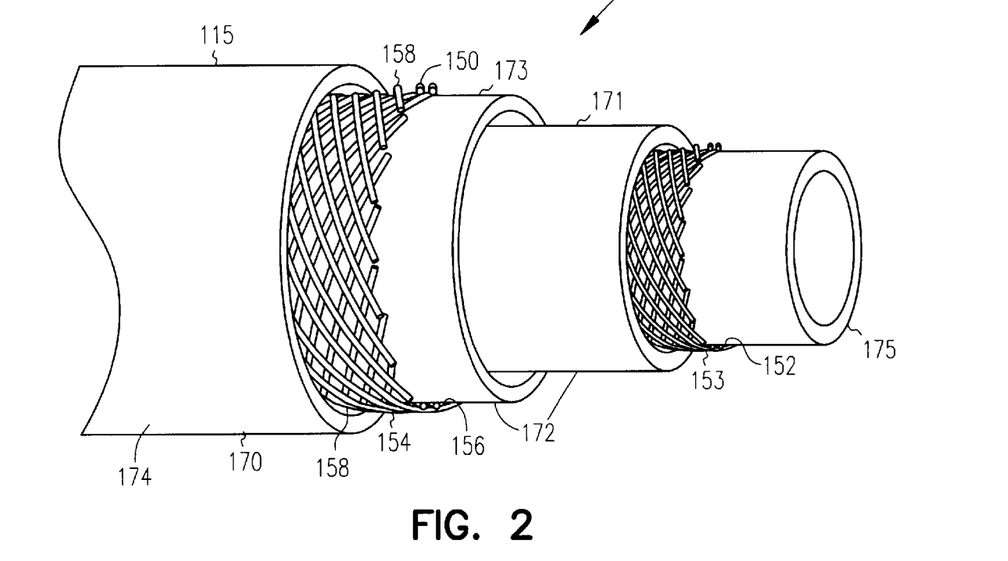
FIG. 2 is a perspective view of a portion of a lead assembly constructed in accordance with one embodiment.
Figure 3:
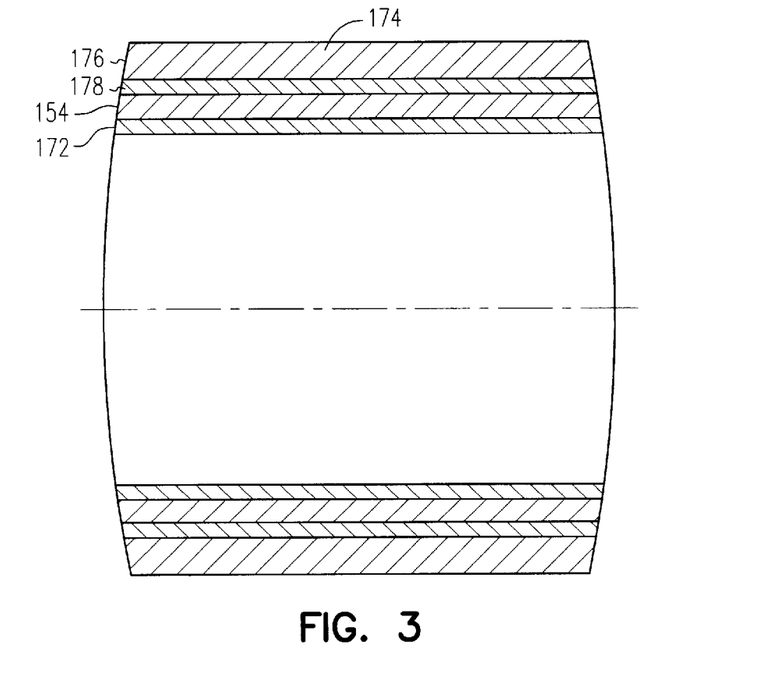
FIG. 3 is a cross-section of a portion of a lead assembly constructed in accordance with one embodiment.

The lead 100 includes a lead body 115, for instance a flexible lead body 115, at least one elongate conductor 150 (FIGS. 2 and 3) contained within the lead body 115, and at least one electrode 120 (FIG. 4) coupled with the lead 100. The lead body 115, as further described below, includes an elongate body formed of, for example, at least one polymer such as a medical grade silicone rubber for translumenal insertion and access within a living organism such as a patient. In one option, the lead body 115 is tubular and has an outer diameter that is small enough for translumenal insertion into the coronary sinus 103 and/or great cardiac vein 105. The at least one electrode 120 is electrically coupled with the elongate conductor 150 (FIGS. 2 and 3). Optionally, the elongate conductor 150 comprises a coiled conductor and defines a lumen therein and thereby is adapted to receive a stiffening stylet that extends through the length of the lead 100. In another option, the elongate conductor 150 comprises a braided conductor, as further described below.

The stylet is used to stiffen the lead 100, and is manipulated to facilitate the insertion of the lead 100 into and through a vein and through an intracardiac valve to advance the distal end 102 of the lead 100 into, for example, the ventricle of the heart 101. Optionally, a stylet knob is coupled with the stylet for rotating the stylet, advancing the conductor into tissue of the heart, and for manipulating the lead 100. Alternatively, the elongate conductor 150 comprises other forms of conductors, such as a cable conductor, or a braided conductor as further discussed below.

FIG. 2 illustrates a portion of the lead shown in FIG. 1, including the lead 100, and/or the lead 100 and the pulse generator and signal sensor 109 (FIG. 1). The lead 100, in one option, is used to chronically stimulate the heart 101 (FIG. 1), such that the lead 100 is implanted on or about the heart 101 (FIG. 1) for long periods of time. As mentioned above, the lead body 115 includes a covering of insulation, and includes at least one elongate conductor 150. In one option, the elongate conductor 150 extends substantially along the entire length between the distal end 102 (FIG. 1) and the proximal end 104 (FIG. 1) of the lead 100. The elongate conductor 150, in one option, includes a first inner conductor 152 and a second conductor 154. In another option, the first inner conductor 152 comprises a cathode of the system 200 (FIG. 1), and the second conductor 154 comprises an anode of the system 200 (FIG. 1).

The first inner conductor 152, in one option, is co-axial but not co-radial with the second conductor 154. For example, the first inner conductor 152 is disposed within the second conductor 154, and an inner layer of insulation 172 is disposed therebetween. The inner layer of insulation 172 is in addition to the lead body 115 which includes at least one outer layer of insulation 170. Optionally, a second inner layer of insulation 175 is disposed within the first inner conductor 152.

The outer layer of insulation 170, in one option, is disposed adjacent to the second conductor 154. The second conductor 154 is defined in part by an inner surface 156 and an outer surface 158. In one option, the outer layer of insulation 170 is disposed directly on the outer surface 158 of the second conductor 154. For instance, the outer layer of insulation 170 is coated directly on the outer surface 158 of the second conductor 154 to form a coating. Examples of coating process include, but are not limited to, spray coating, dipping, brush coating, and vapor deposition. The coating, in one option, comprises a composite coating 174 (FIG. 3) formed of two or more insulative materials. It should be noted that more than two layers of insulative materials could be utilized. In one example, as shown in FIG. 3, the composite coating 174 comprises a first outer coating 176 and a second outer coating 178 of material. In another option, the second outer coating 178 is coated directly on the first outer coating 176. In one option, one of the coatings comprises PTFE, and the other coating comprises polyurethane. Other suitable materials for use with the composite coating 174 include, but are not limited to, silicone or a silicone-urethane hybrid.

Referring again to FIG. 2, the inner layer of insulation 172 is disposed directly on the first inner conductor 152. It should be noted that more than one inner layer of insulation could be incorporated into the lead. The first inner conductor 152 is defined in part by an inner surface and an outer surface 153. As shown in FIG. 2, the inner layer of insulation 172 is disposed directly on the outer surface 153 of the first inner conductor 152. For instance, the inner layer of insulation 172 is coated directly on the outer surface 153 of the first inner conductor 152. Optionally, the inner layer of insulation 172 comprises a composite coating. Suitable materials for the inner layer of insulation 172 include, but are not limited to, PTFE, ETFE, or polyimide.

In one example of the lead 100, the inner layer of insulation 172 comprises a layer which is a minimum of 2 mm thickness, for example, of PTFE. The second conductor 154 comprises a braided conductor, for example having a 3 mm thickness. The first outer coating 176 (FIG. 3) comprises a layer which is a minimum of 2 mm thickness, for example, of PTFE, and the second outer coating 178 (FIG. 3) comprises polyurethane.

Figure 4:
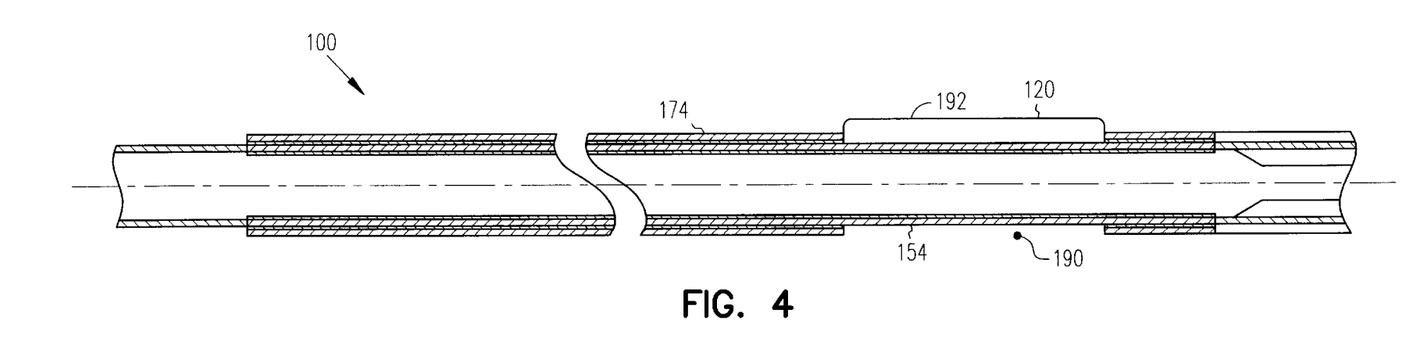
FIG. 4 is a cross-section of a lead assembly constructed in accordance with another embodiment.

Referring to FIG. 4, the lead 100 is shown with a composite outer coating 174 coating directly on the conductor 154. Optionally, a portion 190 of the coating 174 is removed at an intermediate section of the lead 100, and the conductor 154 is exposed. For example, the portion 190 is removed by laser stripping, masking during the coating process, or mechanical stripping. In yet another option, one or more electrodes 192 are electrically and optionally mechanically coupled with the exposed portion 190. For example, the one or more electrodes 192 is welded or swaged with the conductor 154. In another example, the one or more electrodes 192 is crimped or bonded with the conductor 154. The exposed portion 190 allows for the outer body of the lead 100 to be made isodiametrically, which allows for the lead 100 to be more easily inserted into a patient.

Figure 5:
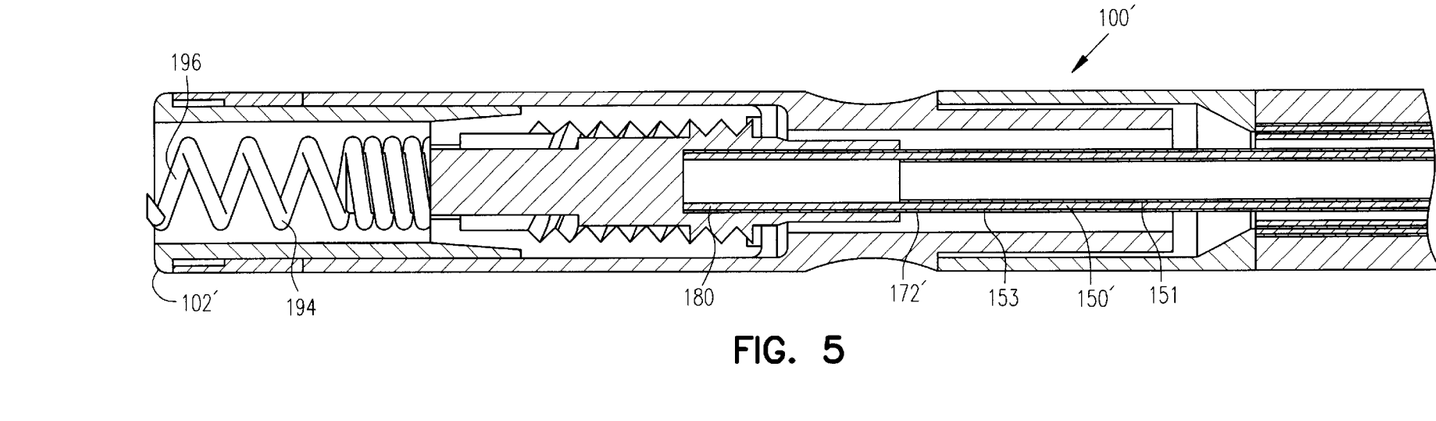
FIG. 5 is a cross-section of a lead assembly constructed in accordance with another embodiment.

FIG. 5 illustrates a distal end 102' of one option of the lead 100'. The lead 100' includes an active fixation device 194 which allows for the distal end 102' of the lead 100' to be fixated with tissue. In one option, the active fixation device 194 comprises a sharpened helical tip 196. In one option, the active fixation device 194 is mechanically coupled directly or indirectly with the conductor 150' such that rotating the conductor 150' rotates the active fixation device 194. In one option, the conductor 150' comprises a braided conductor 151.

The braided conductor 151 is formed of strands of material which are braided together. In one option, the braided conductor 151 is formed of braided strands of flexible material to form a flexible conductor 151. In another option, the braided conductor 151 is formed of metallic flat or metallic round wire. The braided conductor 151 provides for lower resistive properties of the conductor and further provides for improved flex fatigue properties. In another option, the braided conductor 151 comprises a torque transmission member which is formed of conductive or non-conductive material. The conductor 150' comprises a non-coiled conductor of sufficient rigidity to transmit torque provided at the proximal end of the lead to the active fixation device 194 at the distal end of the lead. The torque transmission member allows for torque applied at the proximal end of the lead to be effectively transmitted to the distal end of the lead.

The braided conductor 151 is mechanically coupled to the electrode at 180. In another option, the braided conductor 151 is non-removably coupled to the electrode. For instance, the braided conductor 151 is welded, swaged, crimped, or bonded to the electrode, which is rotatable. In a further option, the electrode comprises an active fixation device 194. In yet another option, the electrode is extendable and/or retractable as the braided conductor 151 is rotated.

The braided conductor 151 is coupled with a proximal end of the lead body, for instance with a connector assembly of the lead. In one option, the braided conductor 151 is mechanically and/or electrically coupled with a terminal pin of the connector assembly, which mates with the pulse generator (FIG. 1). In another option, the braided conductor 151 is welded, bonded, swaged, or crimped with the connector assembly.

In another option, the conductor 150' comprises a coated braided conductor, where the conductor is coated with insulative material, as discussed above. For instance, an inner layer of insulation 172' is coated directly on the outer surface 153 of the conductor 150'. Optionally, the inner layer of insulation 172 comprises a composite coating, including, but not limited to, the various options discussed above. Suitable materials for the inner layer of insulation 172 include, but are not limited to, PTFE, ETFE, or polyimide. The combination of the braided conductor and the coating of insulative material provides for additional strength in transmitting torque from the proximal end to the distal end of the lead.

Figure 6:
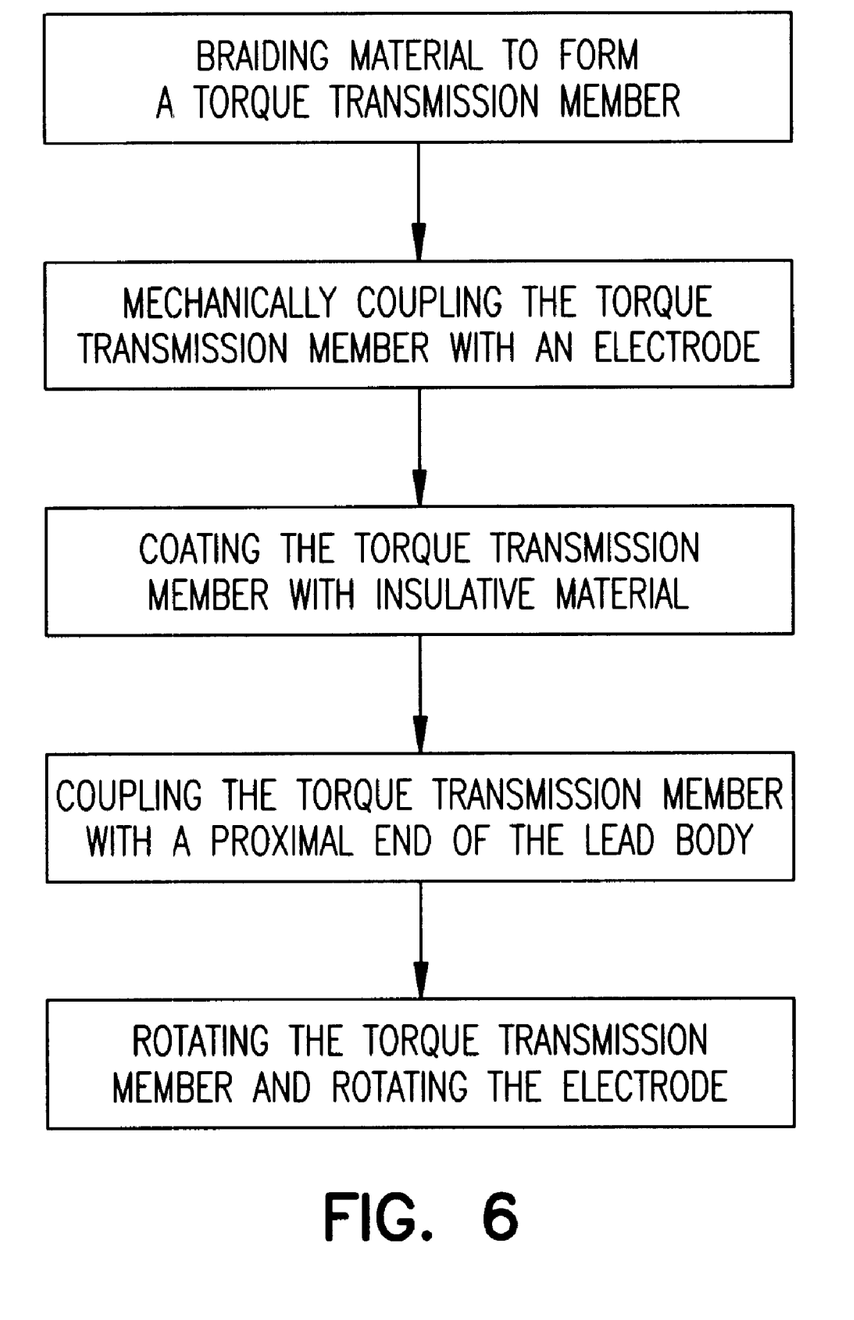
FIG. 6 is a block diagram illustrating a method in accordance with another embodiment.

Referring to FIG. 6, a block diagram is shown illustrating a method. The method includes braiding material to form a torque transmission member, mechanically coupling the torque transmission member with an extendable and/or retractable electrode, disposing the torque transmission member within a flexible lead body, and rotating the torque transmission member and extending at least one electrode.

Several options for the method are as follows. For instance, in one option, the method further includes coating insulative material directly on the torque transmission member. In another option, braiding the material includes braiding conductive material to form an electrically conductive torque transmission member. The method includes, in another option, braiding flexible material to form a flexible torque transmission member. Still further, in another option, the method further includes providing a conductor over and around the torque transmission member, and coating insulative material directly on the conductor.

In another embodiment, a method is provided and includes braiding two or more flexible conductors to form a first flexible, braided conductor, the first braided conductor extending from a first end to a second end. The method further includes coating insulative material directly on the first braided conductor, mechanically and electrically coupling at least one rotatable electrode with the first braided conductor, and disposing the first braided conductor within an outer insulative lead body. The method further includes rotating the first braided conductor and rotating the rotatable electrode, and coupling the first end of the first conductor with an energy source.

Several options for the method are as follows. For instance, the method optionally includes braiding multiple conductors to form a second conductor around the first flexible, braided conductor, and optionally further coating a second coating of insulative material directly on the second braided conductor. In another option, the method includes stripping insulative material from a portion of the first braided conductor, and exposing a portion of the first braided conductor.

Advantageously, the above described lead provides for a smaller lead body diameter due to the elimination of gaps, and tolerance stack-up of the assembly. In addition, the above described device allows for the ability to start and stop tubing to allow for transition areas of the outer insulation, allowing for the device to have an isodiametric shape. Furthermore, the braided conductors have multiple intersections which offer improved flex fatigue properties. A further benefit is that the anode and cathode are not co-radial, the cathode is suitable for use as a driving mechanism for an extendable or retractable positive fixation lead.

Advantageously, the above described lead provides for a smaller lead body diameter due to the elimination of gaps, and tolerance stack-up of the assembly. In addition, the above described device allows for the ability to start and stop tubing to allow for transition areas of the outer insulation, allowing for the device to have an isodiametric shape. Furthermore, the braided conductors have multiple intersections which offer improved flex fatigue properties. A further benefit is that the anode and cathode are not co-radial, the cathode is suitable for use as a driving mechanism for an extendable or retractable positive fixation lead.

It is to be understood that the above description is intended to be illustrative, and not restrictive. For instance, the leads described above include, but are not limited to, tachy, brady, or coronary sinus leads. It should be noted that features of the various above-described embodiments may be interchanged to form additional combinations. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead assembly comprising:
    an insulative lead body extending from a proximal end to a distal end, the lead body including one or more conductors disposed therein, the conductors configured to transmit electric signals through the lead body;
    an electrode assembly including at least one electrode electrically coupled with the one or more conductors; and
    at least one conductor including at least one braided conductor, the braided conductor being coupled to the insulative lead body such that rotating the braided conductor causes the electrode assembly to extend relative to the insulative lead body.

2. The lead assembly as recited in claim 1, further comprising at least one coating of insulation coated directly on the braided conductor.

3. The lead assembly as recited in claim 1, further comprising a second coating of insulation coated between the braided conductor and a second conductor, and the second coating is coated directly on the second conductor.

4. The lead assembly as recited in claim 1, wherein the braided conductor comprises a torque transfer member.

5. A lead assembly comprising:
    a flexible lead body extending from a proximal end to a distal end, the lead body including one or more conductors disposed therein;
    an electrode assembly including at least one electrode electrically coupled with at least one of the conductors; and
    a flexible torque transmission member extending from the proximal end to the distal end, the flexible torque transmission member comprising a braided member that is coupled to the flexible lead body such that rotating the braided member causes the at least one electrode to extend relative to the flexible lead body.

6. The lead assembly as recited in claim 5, wherein the torque transmission member is non-removably disposed within the lead body.

7. The lead assembly as recited in claim 5, further comprising a coating of insulation coated between a first conductor and a second conductor.

8. The lead assembly as recited in claim 7, wherein the coating of insulation is coated directly on the first conductor.

9. The lead assembly as recited in claim 5, further comprising an outer layer of insulative coating, and an inner layer of insulative coating, wherein each insulative coating is coated directly on one of the at least one conductors.

10. The lead assembly as recited in claim 8, further comprising a stripped portion where a portion of the outer layer is stripped from the conductor.

11. A lead assembly comprising:
a flexible, insulative lead body extending from a proximal end to a distal end, the lead body including one or more conductors disposed therein;
an electrode assembly including a first electrode electrically coupled with at least one of the conductors; and
a braided means for transferring torque from the proximal end to a first electrode, the braided means being coupled to the flexible, insulative lead body such that rotating the braided means causes the first electrode to extend relative to the flexible, insulative lead body.

12. The lead assembly as recited in claim 11, wherein the torque transmission member is non-removably disposed within the lead body.

13. The lead assembly as recited in claim 11, wherein the means for transferring torque is operably coupled at the proximal end of the lead body.

14. The lead assembly as recited in claim 11, further comprising a first conductor and a second conductor, and a coating of insulation coated between the first conductor and the second conductor.

15. The lead assembly as recited in claim 11, wherein the braided means for transferring torque comprises an electrical conductor configured to conduct signals from the proximal end to the first electrode.

16. A method comprising:
braiding material to form a torque transmission member;
mechanically coupling the torque transmission member with a rotatable electrode;
disposing the torque transmission member within a flexible lead body;
coupling the torque transmission member to the flexible lead body; and
rotating the torque transmission member cause the rotatable electrode to extend relative to the flexible lead body.

17. The method as recited in claim 16, further comprising coating insulative material directly on the torque transmission member.

18. The method as recited in claim 16, wherein braiding material includes braiding conductive material to form an electrically conductive torque transmission member.

19. The method as recited in claim 16, wherein braiding material includes braiding flexible material to form a flexible torque transmission member.

20. The method as recited in claim 16, further comprising providing a conductor over and around the torque transmission member, and coating insulative material directly on the conductor.

21. The method as recited in claim 16, further comprising coating a first coating of insulative material directly on the torque transmission member, providing a conductor over and around the torque transmission member, and coating a second coating of insulative material directly on the second conductor.

22. A method comprising:
braiding two or more flexible conductors to form a first flexible, braided conductor, the first braided conductor extending from a first end to a second end;
coating insulative material directly on the first braided conductor;
mechanically and electrically coupling at least one rotatable electrode with the first braided conductor;
disposing the first braided conductor within an outer insulative lead body;
coupling the first braided conductor to the outer insulative lead body:
rotating the first braided conductor to rotate extend the rotatable electrode relative to the outer insulative lead body; and
coupling the first end of the first conductor with an energy source.

23. The method as recited in claim 22, further comprising braiding multiple conductors to form a second conductor around the first flexible, braided conductor.

24. The method as recited in claim 23, further comprising coating a second coating of insulative material directly on the second braided conductor.

25. The method as recited in claim 22, further comprising stripping insulative material from a portion of the first braided conductor, and exposing a portion of the first braided conductor.

* * * * *

UNITED STATES PATENT AND TRADEMARK OFFICE
CERTIFICATE OF CORRECTION

PATENT NO. : 6,606,522 B2
DATED : August 12, 2003
INVENTOR(S) : Jon Schell

It is certified that error appears in the above-identified patent and that said Letters Patent is hereby corrected as shown below:

Column 9,
Line 36, delete "cause" and insert -- causing -- therefor.

Column 10,
Line 27, delete "rotate" after "conductor to".
Lines 27-28, delete "extend the rotatable electrode" and insert -- cause the rotatable electrode to extend -- therefor.

Signed and Sealed this

Twenty-third Day of December, 2003

JAMES E. ROGAN
*Director of the United States Patent and Trademark Office*